(12) United States Patent
Royyuru (10) Patent No.: US 8,546,080 B2
(45) Date of Patent: Oct. 1, 2013

(54) MOLECULAR DISPENSERS

(75) Inventor: Ajay K. Royyuru, Congers, NY (US)

(73) Assignee: International Business Machines Corporation, Armonk, NY (US)

( * ) Notice: Subject to any disclaimer, the term of this patent is extended or adjusted under 35 U.S.C. 154(b) by 61 days.

(21) Appl. No.: 13/162,833

(22) Filed: Jun. 17, 2011

(65) Prior Publication Data

US 2012/0322055 A1 Dec. 20, 2012

(51) Int. Cl.
*C12Q 1/68* (2006.01)
*G01N 33/53* (2006.01)
*C12M 1/34* (2006.01)
*C02F 1/40* (2006.01)

(52) U.S. Cl.
USPC .......... 435/6.1; 435/7.1; 435/287.2; 204/600; 977/924

(58) Field of Classification Search
USPC ......... 435/6.1, 7.1, 287.2; 204/600; 977/924
See application file for complete search history.

(56) References Cited

U.S. PATENT DOCUMENTS

| | | | |
|---|---|---|---|
| 5,841,016 A | 11/1998 | Hossain et al. | |
| 6,193,866 B1 | 2/2001 | Bader et al. | |
| 6,627,067 B1 | 9/2003 | Branton et al. | |
| 7,258,838 B2 | 8/2007 | Li et al. | |
| 7,279,337 B2 | 10/2007 | Zhu | |
| 7,410,564 B2 | 8/2008 | Flory | |
| 7,468,271 B2 | 12/2008 | Golovchenko et al. | |
| 2004/0011650 A1 | 1/2004 | Zenhausern et al. | |
| 2005/0123992 A1 | 6/2005 | Volkel et al. | |
| 2006/0068401 A1 | 3/2006 | Flory et al. | |
| 2006/0086626 A1 | 4/2006 | Joyce | |
| 2008/0041733 A1 | 2/2008 | Hibbs et al. | |
| 2008/0171316 A1* | 7/2008 | Golovchenko et al. | ........... 435/6 |
| 2008/0187915 A1 | 8/2008 | Polonsky et al. | |
| 2010/0025249 A1 | 2/2010 | Polonsky et al. | |
| 2010/0291828 A1 | 11/2010 | Reches et al. | |
| 2003/0141189 A1 | 1/2012 | Gazit et al. | |

FOREIGN PATENT DOCUMENTS

WO 2006027780 3/2006

OTHER PUBLICATIONS

Christopher A. Merchant, et al., "DNA Translocation Through Graphene Nanopores," NANO Letters, 10, pp. 2915-2921, 2010.
Utkur M. Mirsaidov, et al., "Molecular Diagnostics for Personal Medicine Using a Nanopore," Advanced Review, Wiley Interdiscip. Rev. Nanomed. Nanobiotechnol. vol. 2, 2010, pp. 367-381.
International Search Report; International Application No. PCT/US 12/37748; International Filing Date: May 14, 2012; Date of Mailing: Sep. 28, 2012; pp. 1-9.
International Search Report—Written Opinion; International Application No. PCT/US 12/37748; International Filing Date: May 14, 2012; Date of Mailing: Sep. 28, 2012; pp. 1-9.
Yuri S. Velichko, et al., "Molecular Dispenser: Conformation-Dependent Design Approach," Macromolecules, vol. 36, No. 14, 5047-5050, 2003.

(Continued)

*Primary Examiner* — Narayan Bhat
(74) *Attorney, Agent, or Firm* — Cantor Colburn LLP; Vazken Alexanian (57) ABSTRACT

A method for dispensing charged particles includes applying a bias voltage to promote motion of charged molecules through a nanopore, detecting passage of at least one charged molecule through the nanopore, and manipulating an electrostatic potential barrier inside the nanopore, so as to prevent movement of additional charged molecules through the nanopore.

12 Claims, 6 Drawing Sheets

(56) References Cited

OTHER PUBLICATIONS

Elejalde, et al., "Real-time, ultralow concentration detection of analytes in solution by infrared intracavity laser absorption," Optical Society of America, vol. 46, No. 19, Applied Optics, pp. 1-5, Jul. 2007.

Helmerson, K. et al., Optical trapping of hydrosomes, Proc. SPIE, 2009.

* cited by examiner

MOLECULAR DISPENSERS

BACKGROUND

The present invention relates generally to nanotechnology, and more specifically, example embodiments of the present invention are directed to nano-scaled apertures configured to accurately transmit individual charged entities, for example, molecules or particles such as beads.

Generally, nano-scaled apertures may be considered nanopores, or apertures on the scale of 1-100 nanometers of internal diameter. Semiconductor nanopores may be produced through a variety of methods, including the formation of an aperture several nanometers to several tens or hundreds of nanometers of internal diameter through a semiconductor substrate. Depending on the desired pore diameter, a variety of techniques may be used to create the pore. For example, electron beam drilling with a transmission electron microscope, reactive ion etching, or ion-beam sculpting may be used to create a pore of specified diameter. The final aperture may be on the scale of 1-100 nanometers, and may be considered a nanopore.

SUMMARY

According to one embodiment of the present invention, a method for dispensing charged particles includes applying a bias voltage to promote motion of charged molecules through a nanopore, detecting passage of at least one charged molecule through the nanopore, and manipulating an electrostatic potential barrier inside the nanopore, so as to prevent movement of additional charged molecules through the nanopore.

According to another embodiment of the present invention, a molecular dispenser includes a molecular reservoir comprising a plurality of charged molecules, a nanopore proximate the molecular reservoir, a first drag electrode arranged within the molecular reservoir, and a control unit. The nanopore comprises a first set of locking electrodes configured to establish an electrostatic potential barrier therein. According to the example embodiment, the control unit is configured to apply an oscillating voltage across the first set of locking electrodes and a bias voltage to the first drag electrode to control flow of individually charged molecules from the molecular reservoir through the nanopore Additional features and advantages are realized through the techniques of the present invention. Other embodiments and aspects of the invention are described in detail herein and are considered a part of the claimed invention. For a better understanding of the invention with the advantages and the features, refer to the description and to the drawings.

BRIEF DESCRIPTION OF THE SEVERAL VIEWS OF THE DRAWINGS

The subject matter which is regarded as the invention is particularly pointed out and distinctly claimed in the claims at the conclusion of the specification. The forgoing and other features, and advantages of the invention are apparent from the following detailed description taken in conjunction with the accompanying drawings in which:

DETAILED DESCRIPTION

Precisely controlling the concentration of a chemical compound (e.g., protein) in a solution is a challenge. Example embodiments provide molecular dispensers which greatly increase the accuracy of control of dispensation through a nanopore structure comprising at least one nanopore. The technical effects and benefits of the nanopore structure include an ability to dispense a precisely controlled count of individual molecules into a desired solution. As used herein, a nanopore refers to a nano-scaled aperture or through-hole entirely penetrating a material, for example, a membrane.

Figure 1:
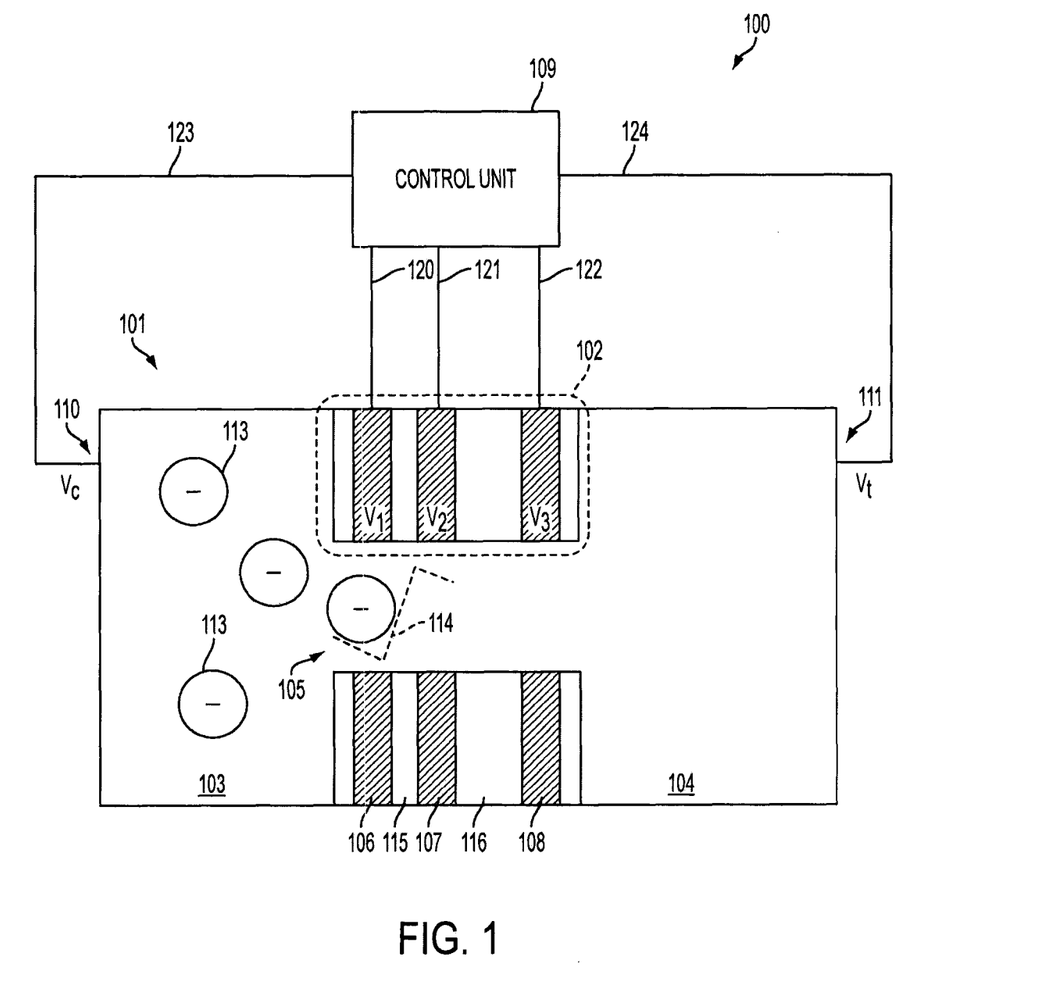
FIG. 1 depicts a schematic cross sectional view of a molecular dispenser, according to an example embodiment.

FIG. 1 is a diagram illustrating a cross-section of a molecular dispenser device, according to an embodiment of the present invention. The device 100 includes a control unit 109 and a nanopore membrane 102 in communication with the control unit. The nanopore membrane 102 may be coated with an electrical insulator such as silicon oxide on both sides of the membrane. The nanopore membrane 102 defines at least one nanopore 105 extending therethrough.

The nanopore membrane 102 includes at least one electrode 106 arranged therein in communication with the control unit 109 via medium 120 (e.g., channel or wire), the at least one electrode 106 further defining the nanopore 105 extending therethrough. For example, the electrode 106 may be substantially planar having a substantially circular hole which defines the nanopore 105. Thus, the interior dimensions of nanopore 105 may be substantially cylindrical, with electrode 106 surrounding the nanopore (e.g., see FIG. 4).

According to the illustrated embodiment, the nanopore membrane 102 may further include an insulating layer 115 proximate the electrode 106, a second electrode 107 proximate the insulating layer 115 and in communication with the control unit 109 via medium 121, a second insulating layer 116 proximate the second electrode 107, and may include a third electrode 108 proximate the second insulating layer 116 and in communication with the control unit 109 via medium 122. The insulating layers may be formed of any suitable insulator, including silicon dioxide, for example. The electrodes may be formed of any suitable electrically conducting material or metal.

By way of illustration, FIG. 1 depicts an arrangement of the device 100 for transferring a charged entity or charged molecule 113 from a molecular reservoir portion 103 (preceding the nanopore) to a target solution portion 104 (following the nanopore). The membrane 102 is formed as a stack of the electrodes 106, 107, 108 separated by the insulating layers 115 and 116. The electrical potential of each electrode ($V_1$, $V_2$, and $V_3$) is set independently by control unit 109. Electrodes 106 and 107 are referred to as locking electrodes herein. Electrode 108 is referred to as a counter or detector electrode herein. $V_1$, $V_2$, $V_3$ are the respective voltages for electrodes 106, 107, 108.

Portion 103 and portion 104 are connected by a nanopore 105 in the nanopore membrane 102. Locking electrodes (for example, 106 and 107) are capable of creating an electrostatic potential barrier 114 inside the nanopore 105 by, for example, creating a potential difference between the electrodes to impede flow through the nanopore 105.

Control unit 109 provides bias voltage ($V_c$) to electrode 110 in portion 103 via electrical communication medium 123, and also provides bias voltage ($V_t$) to electrode 111 in portion 104 via electrical communication medium 124. Electrodes 110 and 111 are referred to as drag electrodes. The drag electrodes may be formed of any suitable electrically conducting material or metal, including silver. The drag electrodes may be fixed in space within respective portions 103 and 104, or may be positioned relatively proximate an entry and exit of the nanopore 105. The drag electrodes may be biased to compel movement of the charged molecules 113 through the nanopore 105.

Charged molecules 113 may be, for example, originally located in molecular reservoir portion 103. The voltage difference $V_t - V_c$ (drag voltage) attracts the charged molecules towards portion 104. Control unit 109 detects the passage of a charged molecule inside the nanopore 105. The detection can be accomplished, for example, by measuring the variation of ion current between drag electrodes 110 and 111, locking electrodes 106 and 107, and/or counter electrode 108. According to an example embodiment, passage detection is facilitated by detection of a variation of voltage or current at the counter electrode 108. According to other example embodiments, passage detection is facilitated by measurement between drag electrode 110 and drag electrode 111 singularly or in combination with measurement from counter electrode 108. It is to be appreciated, however, that measurements can also made using any combination of locking, counter, and drag electrodes.

Upon or prior to passage of a molecule within the nanopore 105, locking voltages are applied to locking electrodes (for example, 106, 107) to create the potential barrier 114. The potential barrier 114 may be oscillated in a ratcheting manner to compel sequential passage of individual charged molecules through the nanopore 105 by application of time-dependent voltage biases to the locking electrodes 106 and 107. Upon passage of a desired number of charged molecules, the bias voltages of the drag electrodes 110 and 111 may be removed. The drag electrodes and locking electrodes can be controlled independently, or can be controlled in parallel, for example, through use of simple logic gates with the application of at least one oscillating control signal.

As illustrated, three electrodes are used within the electrode stack of the membrane 102. It is to be appreciated, however, that one or more locking electrodes may be used in other embodiments. In an embodiment where a single locking electrode is used, a potential barrier is created as a result of the voltage of the locking electrode. For example, a locking electrode with a voltage of 0.4 Volt may create a potential barrier in a surrounding environment of neutral voltage or a drag voltage of 0.8 Volt. Furthermore, a plurality of potential barriers may be produces through use of multiple electrodes stacked through the length of a nanopore.

In FIG. 1, locking electrodes 106, 107 and 108 are shown to have cylindrical geometry (for example, metal plane with a hole therethrough). In other embodiments of the present invention, however, the geometry of the locking electrodes and drag electrodes can vary. By way of example, an example embodiment may include two electrodes per layer, each occupying a portion of a half plane with a hole in the center.

As illustrated, example embodiments may include the control unit 109. It is to be appreciated, however, that other embodiments may include one or more control units. A control unit may include, for example, a computer that connects to a specialized board with an application-specific integrated circuit (ASIC), wherein the board connects to the device. A control unit may also, for example, be integrated with the device by way of a Nano-Electro-Mechanical System (NEMS), wherein a nanofluidics portion (for example, a reservoir of charged molecules) can be combined with electronics (for example, a control unit). The control unit applies bias voltages to the drag electrodes to attract a charged molecule from a molecular reservoir portion of a reservoir to a target solution portion of a reservoir, as well as applying a time-dependent or oscillating voltage to each locking electrode to create an electrostatic potential barrier, wherein the electrostatic potential barrier controls the passage of individual charged molecules through a nanopore.

Moreover, in an example embodiment of the present invention, the control unit implements detection of entry of the charged molecule inside the nanopore, and altering the time-dependent voltages from the locking electrodes.

Also, in one or more embodiments of the present invention, the control unit may implement repetition of one or more actions. Such actions may include, for example, reducing or removing the bias voltages from the drag electrodes, and increasing or re-applying the time-dependent voltage to each locking electrode to create and manipulate an electrostatic potential barrier in a ratcheting manner. Such repeated actions may also include, for example, performing one or more characterization activities of a target solution including individual molecule counting and resolution, reducing or removing the time-dependent voltage from each locking electrode and the electrostatic potential barrier, and increasing or re-applying the bias voltages to the drag electrodes to transfer the charged molecules from the molecular reservoir 103 to the target solution 104.

In an illustrative embodiment of the invention, the control unit implements repetition of the above steps until a desired or target composition of a target solution is reached.

Although illustrated and described above as including a single potential barrier, it should be appreciated that the same may be varied to further increase the molecular dispensing accuracy of example embodiments. For example, FIG. 2 is a diagram illustrating a cross-section of a molecular dispenser device implementing a plurality of potential barriers, according to an embodiment of the present invention.

The device 200 includes a control unit 209 and a nanopore membrane 202 in communication with the control unit. The nanopore membrane 202 defines at least one nanopore 205 extending therethrough. The nanopore membrane 202 includes electrodes 206, 207, 208, 241, 242, and 243 arranged therein in communication with the control unit 209 via mediums 220, 221, 222, 230, 231, and 232 (e.g., channels or wires). Each electrode further defines the nanopore 205 extending therethrough. For example, the electrodes may be substantially planar having a substantially circular hole which defines the nanopore 205. Thus, the interior dimensions of nanopore 205 may be substantially cylindrical, with electrodes surrounding the nanopore (e.g., see FIG. 4).

According to the illustrated embodiment, the nanopore membrane 202 may further include insulating layers 215, 216, 217, 218, and 219 arranged between adjacent electrodes forming an electrode stack somewhat similarly as in FIG. 1. The insulating layers may be formed of any suitable insulator, including silicon dioxide, for example. The electrodes may be formed of any suitable electrically conducting material or metal.

Figure 2:
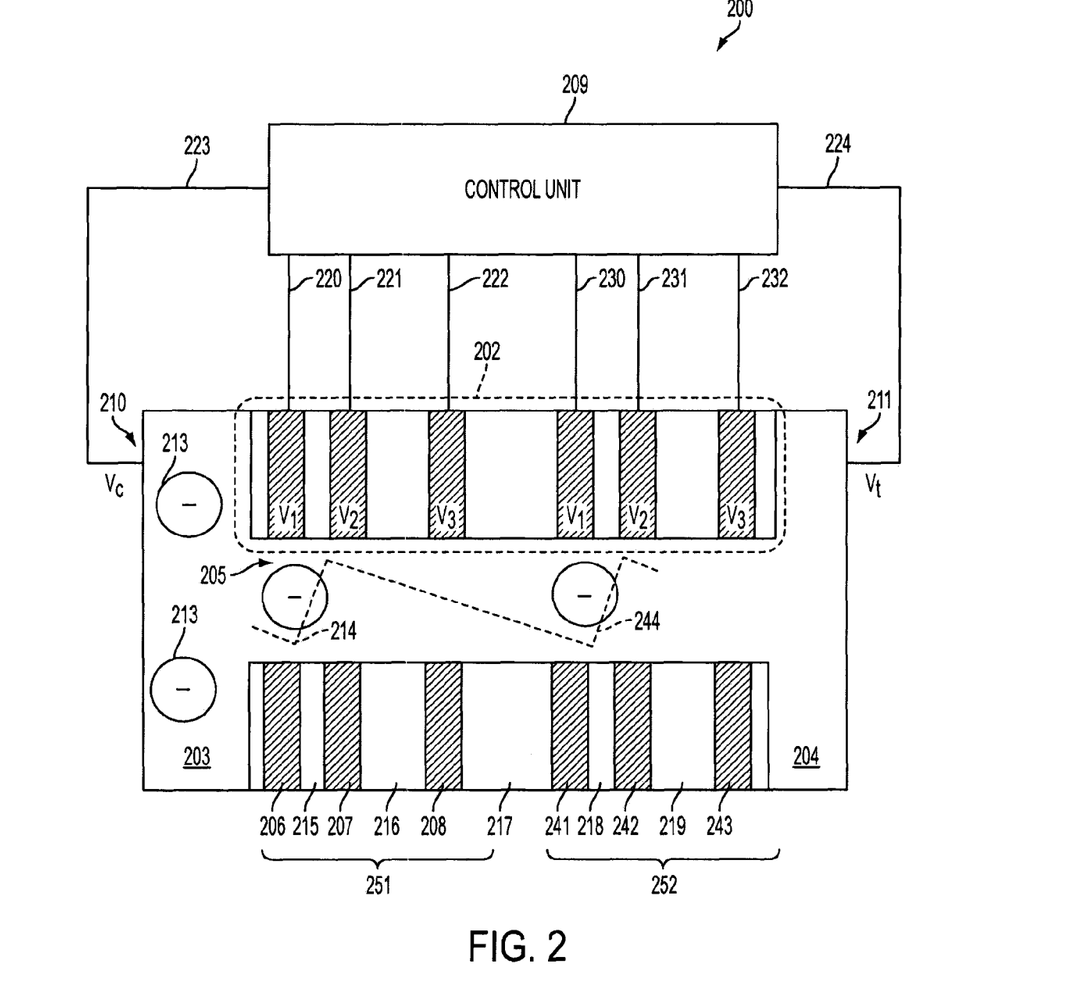
FIG. 2 depicts a schematic cross sectional view of a molecular dispenser, according to an example embodiment.

By way of illustration, FIG. 2 depicts an arrangement of the device 200 for transferring a charged molecule 213 from a molecular reservoir portion 203 (preceding the nanopore) to a target solution portion 204 (following the nanopore) more accurately as compared to the device 100. The electrical potential of each electrode ($V_1$, $V_2$, $V_3$, $V_4$, $V_5$, and $V_6$) is set independently by control unit 209. Electrodes 206, 207, 241, and 242 are referred to as locking electrodes herein. Electrodes 208 and 243 referred to as counter or detector electrodes herein. Furthermore, electrodes 206, 207, and 208 may be grouped and referred to as a first set of ratcheting/locking electrodes 251, while electrodes 241, 242, and 243 may be grouped and referred to as a second set of ratcheting/locking electrodes 252.

Portion 203 and portion 204 are connected by the nanopore 205 in the nanopore membrane 202. Locking electrodes (for example, 206, 207, 241, and 242) are capable of creating electrostatic potential barriers 214 and 244 inside the nanopore 205 by, for example, creating a potential difference between the electrodes to impede flow through the nanopore 205.

Control unit 209 provides bias voltage ($V_c$) to electrode 210 in portion 203 via electrical communication medium 223, and also provides bias voltage ($V_t$) to electrode 211 in portion 204 via electrical communication medium 224. Electrodes 210 and 211 are referred to as drag electrodes. The drag electrodes may be formed of any suitable electrically conducting material or metal, including silver. The drag electrodes may be fixed in space within respective portions 203 and 204, or may be positioned relatively proximate an entry and exit of the nanopore 205. The drag electrodes may be biased to compel movement of the charged molecules 213 through the nanopore 205.

Charged molecules 213 may be, for example, originally located in molecular reservoir portion 203. The voltage difference $V_t - V_c$ (drag voltage) attracts the charged molecules towards portion 204. Control unit 209 detects the passage of a charged molecule inside the nanopore 205. The detection can be accomplished, for example, by measuring the variation of ion current between drag electrodes 210 and 211, locking electrodes 206, 207, 241, 242, and/or counter electrodes 208 and 243. According to an example embodiment, passage detection is facilitated by the counter electrodes 208 and 243. According to other example embodiments, passage detection is facilitated by measurement between drag electrode 210 and drag electrode 211 singularly or in combination with measurement from counter electrodes 208 and 241. It is to be appreciated, however, that measurements can also made using any combination of locking, counter, and drag electrodes.

Upon or prior to passage of a molecule within the nanopore 205, locking voltages are applied to locking electrodes to create the potential barrier 214. The potential barrier 214 may be oscillated in a ratcheting manner to compel sequential passage of individual charged molecules through the nanopore 205 by application of time-dependent voltage biases to first set of ratcheting/locking electrodes 251. Upon passage of a single charged molecule past the counter electrode 208, time-dependent voltage biases may be applied to the second set of ratcheting/locking electrodes 252, while a locking voltage is applied to the locking electrodes 206 and 207. In this manner, a single charged molecule may be passed through a dual-ratchet arrangement of potential barriers, thereby increasing the effectiveness of the device 200 as compared to the device 100 with regards to passage of single molecules through a nanopore.

Upon passage of a desired or target number of molecules through the nanopore 205, the bias voltages of the drag electrodes 210 and 211 may be removed. The drag electrodes and locking electrodes (e.g., individual sets of ratcheting electrodes) can be controlled independently, or can be controlled in parallel, for example, through use of simple logic gates with the application of at least one oscillating control signal.

According to an example embodiment of the present invention, at least two oscillating signals are applied, a first oscillating signal being applied to the first set of ratcheting/locking electrodes 251, and a second oscillating signal being applied to the second set of ratcheting/locking electrodes 252. According to this embodiment, the frequencies of the first and second oscillating signals may be different, with one operating at a higher frequency.

Figure 3:
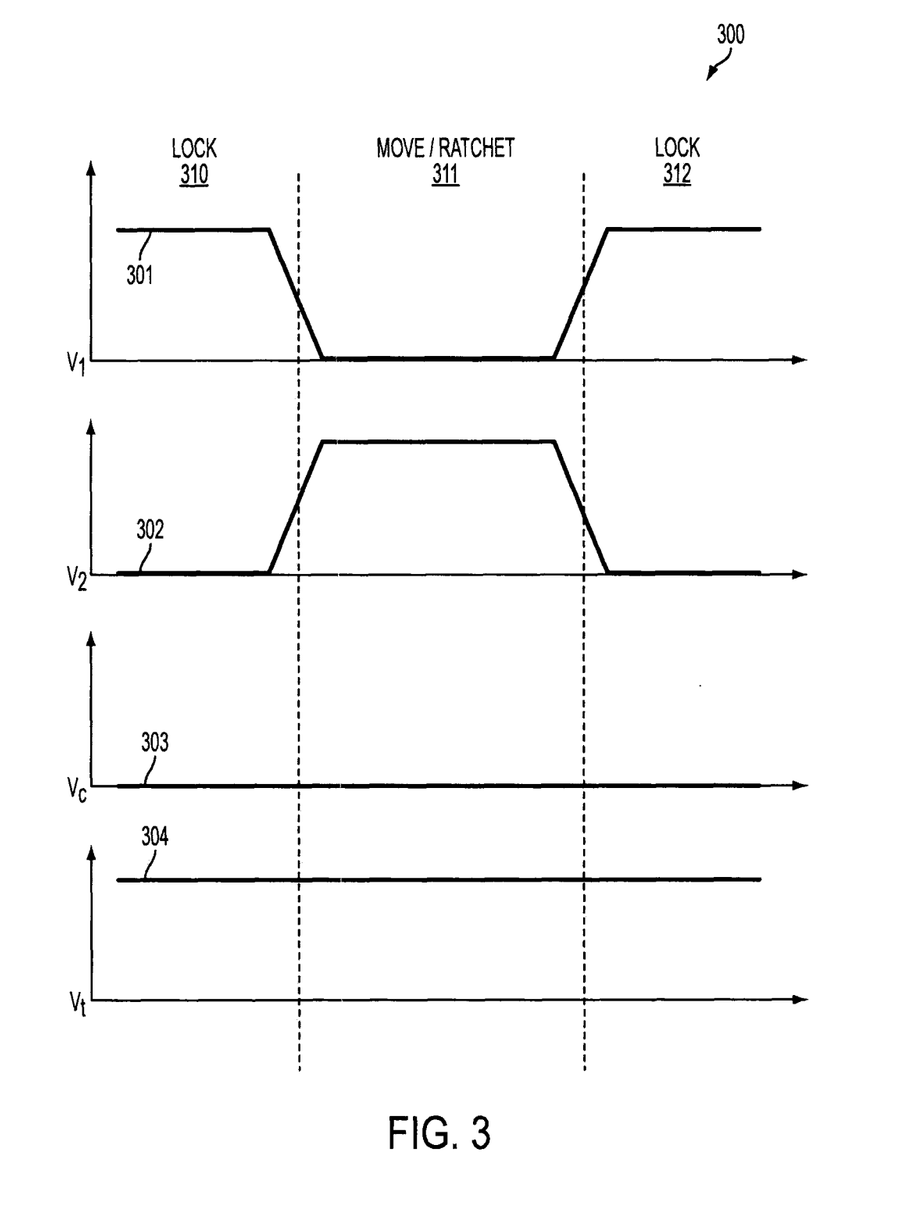
FIG. 3 depicts a graph of time-dependent ratcheting voltages of a molecular dispenser, according to an example embodiment.

In order to better understand the creation of a potential barrier for oscillation in a ratcheting manner, FIG. 3 is provided. FIG. 3 is a diagram illustrating example applications of time-dependent voltages, according to an embodiment of the present invention. By way of illustration, FIG. 3 depicts three positions, a lock position 310, a move position 311, and a lock position 312, of the device arrangement illustrated in FIG. 1. It should be appreciated that the same voltage bias information is easily extensible to the dual-ratchet arrangement of FIG. 2. As shown, the bias voltage 301 of electrode 106 oscillates from a positive value to a lower value and the bias voltage 302 of the electrode 107 oscillates from a neutral value to a positive value in order to disable the potential barrier 114. Further, steady application of a bias voltage to the electrodes 110 and 111 (e.g., voltages 303-304) results in a steady electrostatic force compelling motion of the charged particles towards and through a nanopore, being impeded only by oscillation of the voltages 301 and 302 to a lock position.

Figure 4:
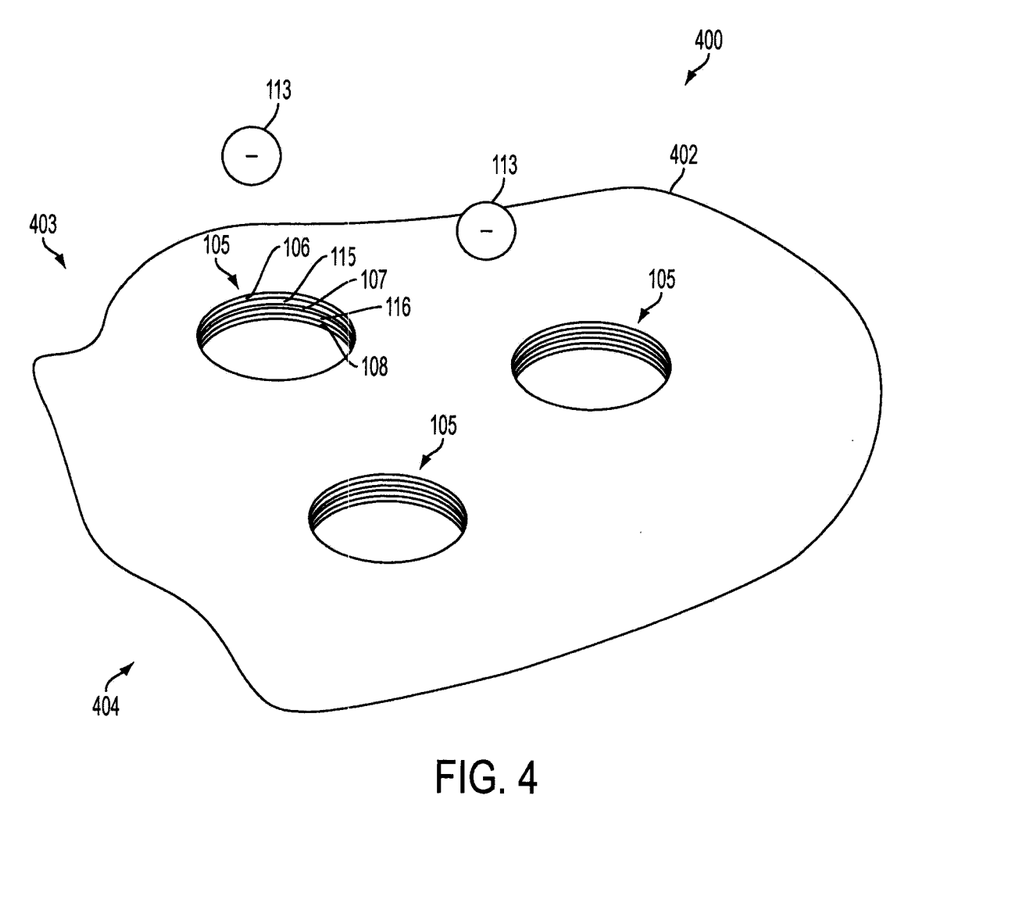
FIG. 4 depicts a perspective view of molecular dispenser sieve, according to an example embodiment.

It should be readily appreciated that while described singularly, nanopores are useable in combination, such as, for example, in a nano-sieve as illustrated in FIG. 4. As shown, the sieve 400 includes a nanopore membrane 402 comprising a plurality of nanopores 105, each under the control of an independent or combined control unit. Alternatively, the nanopore membrane may also include additional nanopores of different design, for example, including nanopores 205. As depicted, the sieve 400 provides a barrier between reservoirs 403 and 404, such that very precise control over passage of charges molecules 113 is possible.

It should be readily appreciated that sieve 400 may comprise a plurality of nanopores of different sizes (e.g., diameters, depths, etc) for the separation and organization of molecules by size and charge.

It should further be appreciated that sieve 400 may enable the precise determination of molecular density or quantity of a solution through counting of molecules passing through respective nanopores of the sieve 400.

It should further be appreciated that sieve 400 may be scaled to millions of nanopores operating simultaneously and independently to provide a faster result.

It should further be appreciated that a plurality of sieves 400 may be used in a system for dispensing molecules. Each sieve of the plurality of sieves may be configured to transport molecules of a different type to a single target solution, thereby facilitating formation of complex but accurate mixtures of molecules.

It should further be appreciated although particularly described as transferring charged molecules only, polymer capsules with a net electrical charge may be used to facilitate transfer of electrically-neutral payloads.

As described above, molecular dispensers are provided which significantly increase the accuracy of creating or measuring solutions through the restricted passage of molecular compounds through one or more nanopores. Each nanopore may include at least one electrode configured to provide an electrostatic potential barrier to passage of molecules therethrough. Furthermore, adjacent reservoirs, a molecular reservoir comprising suspended molecules and a target solution reservoir for creation of a target solution, may be electrically biased such that molecules from the molecular reservoir are compelled to motion towards and through the one or more nanopores. Moreover, ratcheting application of a time-dependent voltage on the at least one electrode provides a ratcheting action to transport molecules in a singular, sequential manner from the molecular reservoir to the target solution reservoir.

Hereinafter, a more detailed description of methodologies of molecular dispensing are described with references to FIGS. 5-6.

Figure 5:
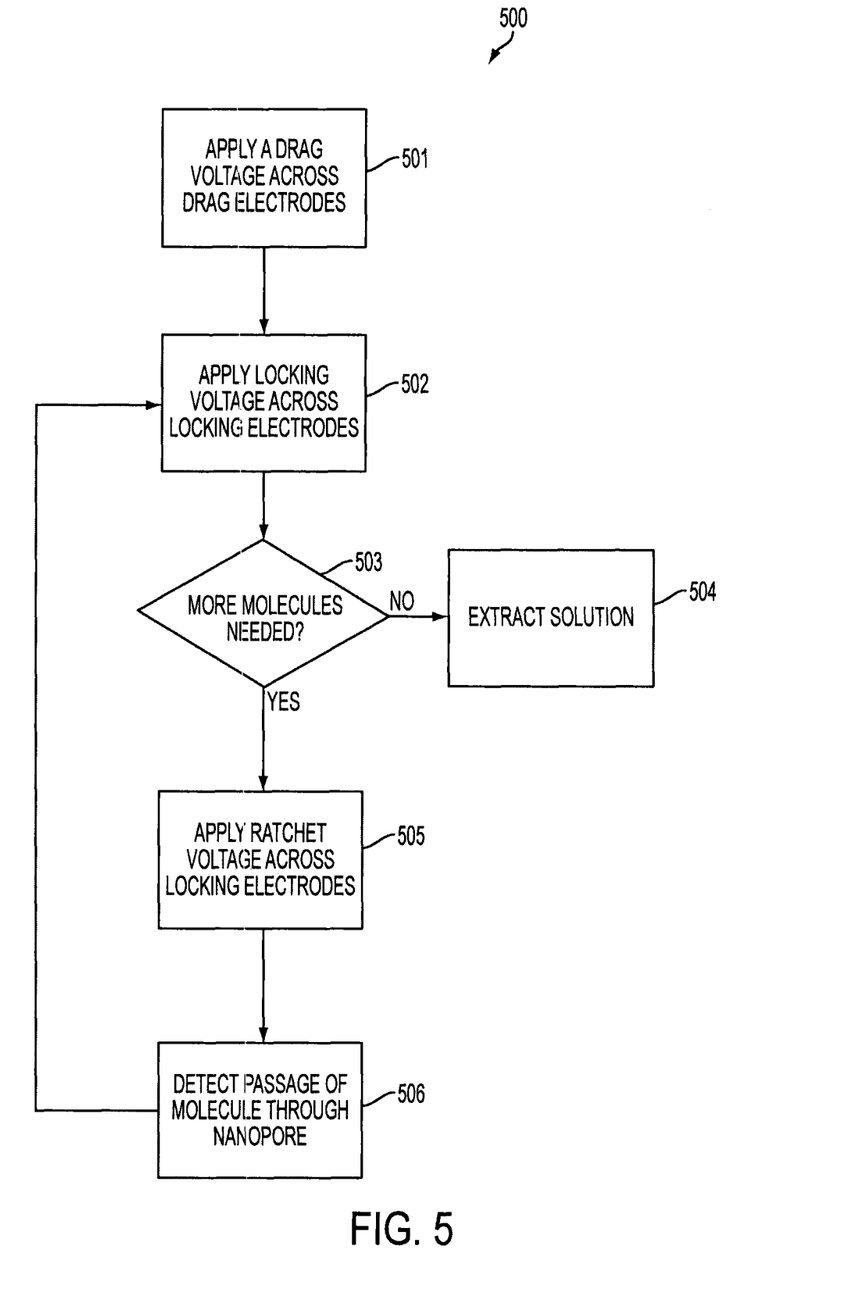
FIG. 5 is a flow diagram illustrating a method of dispensing molecules, according to an example embodiment.

Turning to FIG. 5, the method 500 includes applying a drag voltage across drag electrodes of a molecular dispenser at block 501. The drag voltage may be any amount of voltage suitable for compelling motion of suspended molecules through a nanopore. The molecular dispenser may be any suitable dispenser comprising a control unit and at least one nanopore arranged to transfer molecules. The drag electrodes may be suspended in adjacent solution reservoirs, for example, a molecular reservoir and a target solution reservoir, and may be biased by the control unit.

The method 500 further includes applying a locking voltage across locking electrodes of the molecular dispenser at block 502. The locking voltage may be a voltage bias greater than or equal to a surrounding electrostatic potential, for example, such that application of the locking voltage forms an electrostatic potential barrier proximate the locking electrodes and within the nanopore, which blocks transfer of molecules therethrough (e.g., see. FIG. 3.)

The method 500 further includes determining if more molecules are needed in the target solution reservoir at block 503. If more molecules are needed, the method 500 includes applying a move/ratcheting voltage across the locking electrodes at block 505. The ratcheting voltage may be a voltage bias sufficient to allow travel of a molecule, or a voltage bias configured to push a molecule through a portion of the nanopore. The method 500 further includes detecting passage of a molecule through the at least one nanopore at block 506. For example, detection may be facilitated through the control unit by detecting voltage variations across the drag electrodes and/or through use of a counter electrode arranged around the nanopore. Thereafter, the method returns to block 502 for additional ratcheting as described above.

If more molecules are not needed as determined at block 503, the target solution may be extracted or otherwise used at block 504. It should be appreciated that this method of molecular dispensing is also reversible, for removal of molecules from the target solution reservoir, through application of reverse voltage bias. Moreover, it should also be understood that block 503 is easily replaceable with any suitable decision, for example, if using the molecular dispenser as an analysis tool to count available molecules from the molecular reservoir.

As described above, molecular dispensers are not limited to dispensers including nanopores with a single set of ratcheting/locking electrodes. For example, according to some example embodiments (e.g., FIG. 2), nanopores may include two or more sets of ratcheting/locking electrodes.

Figure 6:
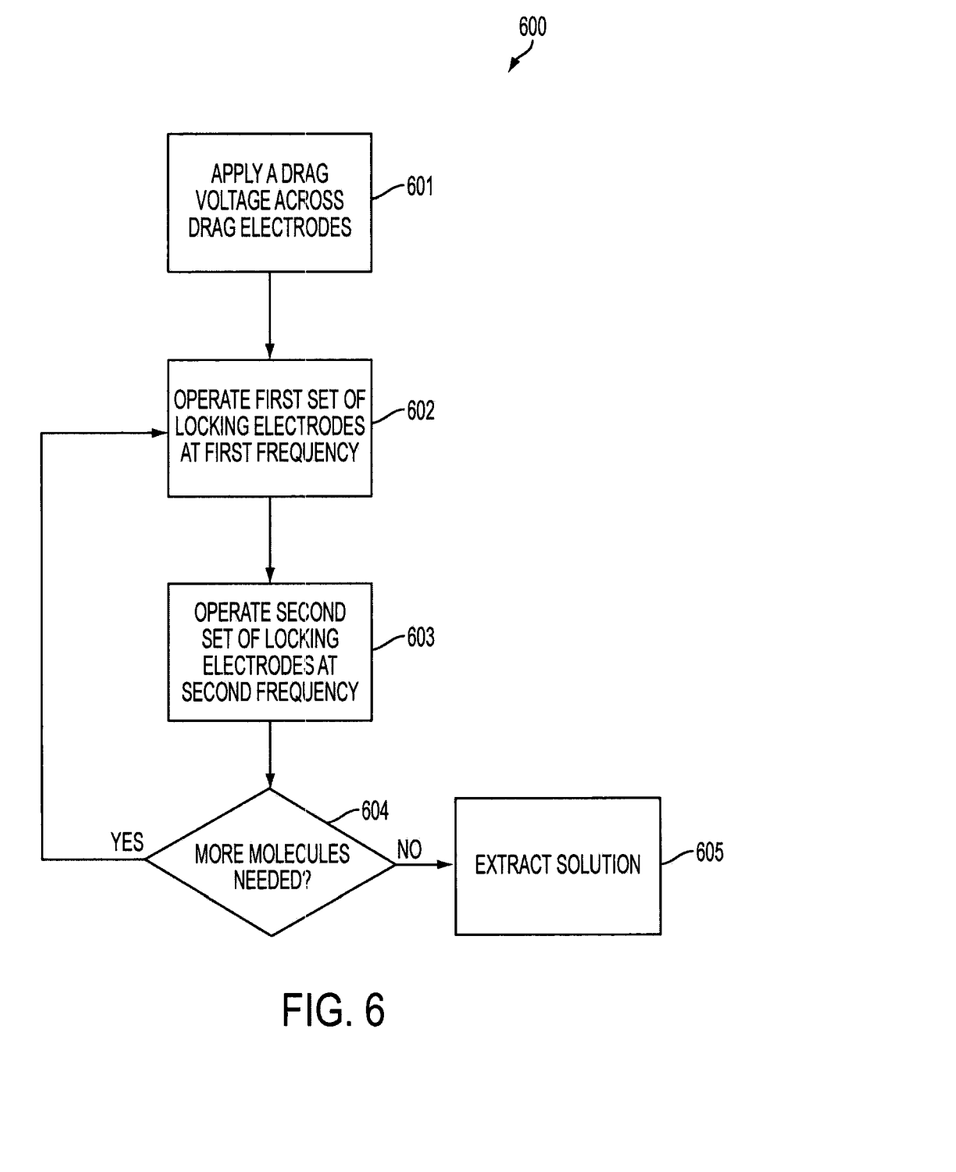
FIG. 6 is a flow diagram illustrating a method of dispensing molecules, according to an example embodiment.

Turning to FIG. 6, a method of dispensing molecules is illustrated. The method 600 includes applying a drag voltage across drag electrodes of a molecular dispenser at block 601. The drag voltage may be any amount of voltage suitable for compelling motion of suspended molecules through a nanopore. The molecular dispenser may be any suitable dispenser comprising a control unit and at least one nanopore arranged to transfer molecules (e.g., dispenser 200). The drag electrodes may be suspended in adjacent solution reservoirs, for example, a molecular reservoir and a target solution reservoir, and may be biased by the control unit.

The method 600 further includes operating a first set of locking electrodes at a first frequency at block 602 (e.g., at a first oscillating voltage), and operating a second set of locking electrodes at a second frequency at block 603 (e.g., at a second oscillating voltage). Operating the first set of locking electrodes includes performing method steps 502-506 for the first set of locking electrodes at the first frequency. For example, by oscillating from a first locking voltage and first ratcheting voltage at the first frequency. Similarly, operating the second set of electrodes at the second frequency includes performing method steps 502-506 for the second set of locking electrodes at the second frequency. For example, by oscillating from a second locking voltage and second ratcheting voltage at the second frequency. According to one example embodiment, the first frequency and the second frequency are the same frequency. According to another example embodiment, the first frequency and the second frequency are different. According to another example embodiment, the first frequency is lower than the second frequency. According to another example embodiment, the first frequency and the second frequency are out of phase, such that the first set of locking electrodes are locked if the second set of locking electrodes are open (e.g., no potential barrier applied), and vice versa.

Turning back to FIG. 6, the method 600 further includes determining if more molecules are needed in the target solution reservoir at block 604. If more molecules are not needed, the target solution may be extracted or otherwise utilized at block 605.

It is noted that the terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There may be many variations to this diagram or the steps (or operations) described therein without departing from the spirit of the invention. For instance, the steps may be performed in a differing order or steps may be added, deleted or modified. All of these variations are considered a part of the claimed invention.

While particular embodiments of the invention have been described, it will be understood that those skilled in the art, both now and in the future, may make various improvements and enhancements which fall within the scope of the claims which follow. These claims should be construed to maintain the proper protection for the invention first described.

What is claimed is:

1. A method for dispensing charged particles, comprising:
applying a bias voltage to promote motion of charged molecules through a nanopore;
detecting passage of at least one charged molecule through the nanopore;
oscillating an electrostatic potential barrier inside the nanopore, so as to prevent movement of additional charged molecules through the nanopore; and
oscillating a second electrostatic potential barrier inside the nanopore, wherein the second electrostatic potential barrier blocks movement of the charged molecule through the nanopore, and wherein the second electrostatic potential barrier is arranged separate from the electrostatic potential barrier.

2. The method of claim 1, wherein detecting passage of the at least one charged molecule comprises measuring a variation of ion current between drag electrodes.

3. The method of claim 1, wherein detecting passage of the at least one charged molecule comprises measuring a variation of voltage or current at a counter electrode arranged proximate the nanopore.

4. The method of claim 1, wherein oscillating the electrostatic potential barrier comprises:
applying a locking voltage across locking electrodes arranged proximate the nanopore.

5. The method of claim 4, wherein the locking voltage is of the same polarity as the bias voltage.

6. The method of claim 4, wherein oscillating the electrostatic potential barrier further comprises:
determining if more molecules should be dispensed; and
applying a ratcheting voltage across the locking electrodes in response to the determining.

7. The method of claim 1, wherein oscillating the electrostatic potential barrier comprises:
oscillating a voltage across locking electrodes arranged proximate the nanopore between a locking voltage and a ratcheting voltage.

8. The method of claim 1, wherein:
oscillating the electrostatic potential barrier comprises applying a first locking voltage across a first set of locking electrodes arranged proximate the nanopore; and
oscillating the second electrostatic potential barrier comprises applying a second locking voltage across a second set of locking electrodes arranged proximate the nanopore.

9. The method of claim 8, wherein the first locking voltage is of the same polarity as the bias voltage, and wherein the second locking voltage is of the same polarity as the bias voltage.

10. The method of claim 8, wherein:
oscillating the electrostatic potential barrier further comprises applying a first ratcheting voltage across the first set of locking electrodes; and
oscillating the second electrostatic potential barrier further comprises applying a second ratcheting voltage across the second set of locking electrodes.

11. The method of claim 1, wherein:
oscillating the electrostatic potential barrier comprises oscillating a voltage across a first set of locking electrodes arranged proximate the nanopore between a first locking voltage and a first ratcheting voltage; and
oscillating the second electrostatic potential barrier comprises oscillating a voltage across a second set of locking electrodes arranged proximate the nanopore and separate the first set of locking electrodes between a second locking voltage and a second ratcheting voltage.

12. The method of claim 1, further comprising:
oscillating a second electrostatic potential barrier inside the nanopore, wherein the second electrostatic potential barrier blocks movement of the charged molecule through the nanopore, and wherein the second electrostatic potential barrier is oscillated out of phase with the electrostatic potential barrier.

* * * * *